United States Patent
Jain et al.

(10) Patent No.: US 9,165,114 B2
(45) Date of Patent: Oct. 20, 2015

(54) METHOD AND SYSTEM FOR CHARACTERIZING AND VISUALIZING ELECTROMAGNETIC TRACKING ERRORS

(75) Inventors: Ameet Kumar Jain, New York, NY (US); Mohammad Babak Matinfar, Baltimore, MD (US); Raymond Chan, San Diego, CA (US); Vijay Parthasarthy, Tarrytown, NY (US); Douglas A. Stanton, Ossining, NY (US)

(73) Assignee: Koninklijke Philips N.V., Eindhoven (NL)

( * ) Notice: Subject to any disclaimer, the term of this patent is extended or adjusted under 35 U.S.C. 154(b) by 279 days.

(21) Appl. No.: 13/582,062

(22) PCT Filed: Feb. 21, 2011

(86) PCT No.: PCT/IB2011/050706
§ 371 (c)(1),
(2), (4) Date: Aug. 31, 2012

(87) PCT Pub. No.: WO2011/110966
PCT Pub. Date: Sep. 15, 2011

(65) Prior Publication Data
US 2012/0323111 A1    Dec. 20, 2012

Related U.S. Application Data

(60) Provisional application No. 61/312,807, filed on Mar. 11, 2010.

(51) Int. Cl.
A61B 5/055    (2006.01)
G06F 19/00    (2011.01)
A61B 19/00    (2006.01)
A61B 17/00    (2006.01)

(52) U.S. Cl.
CPC ........ *G06F 19/3437* (2013.01); *A61B 19/5244* (2013.01); *A61B 2017/00119* (2013.01); *A61B 2019/5251* (2013.01)

(58) Field of Classification Search
CPC ............ G06F 19/3437; A61B 19/5244; A61B 2019/5251; A61B 2017/00119
See application file for complete search history.

(56) References Cited

U.S. PATENT DOCUMENTS

2005/0107687 A1    5/2005    Anderson
2008/0183064 A1    7/2008    Chandonnet et al.

FOREIGN PATENT DOCUMENTS

WO    WO2007113719    10/2007

OTHER PUBLICATIONS

Matinfar et al., "Absolute vs. Relative Error Characterization of Electromagnetic Tracking Accuracy". Proc. SPIE 7625, Medical Imaging 2010: Visualization, Image-Guided Procedures, and Modeling, 762524 (Feb. 24, 2010).*

*Primary Examiner* — Long V Le
*Assistant Examiner* — Colin T Sakamoto

(57) ABSTRACT

A calibration/surgical tool includes an electromagnetic sensor array of two or more electromagnetic sensors in a known geometrical configuration. Electromagnetic tracking errors are characterized by a mapping of pre-operative absolute and relative errors based on a movement of a calibrated calibration/surgical tool through a pre-operative electromagnetic field. Using statistical mapping, a desired absolute error field is measured either in the clinic as the part of daily quality control checks, or before the patient comes in or in vivo. A resulting error field may be displayed to the physician to provide clear visual feedback about measurement confidence or reliability of localization estimates of the absolute errors in electromagnetic tracking.

20 Claims, 14 Drawing Sheets

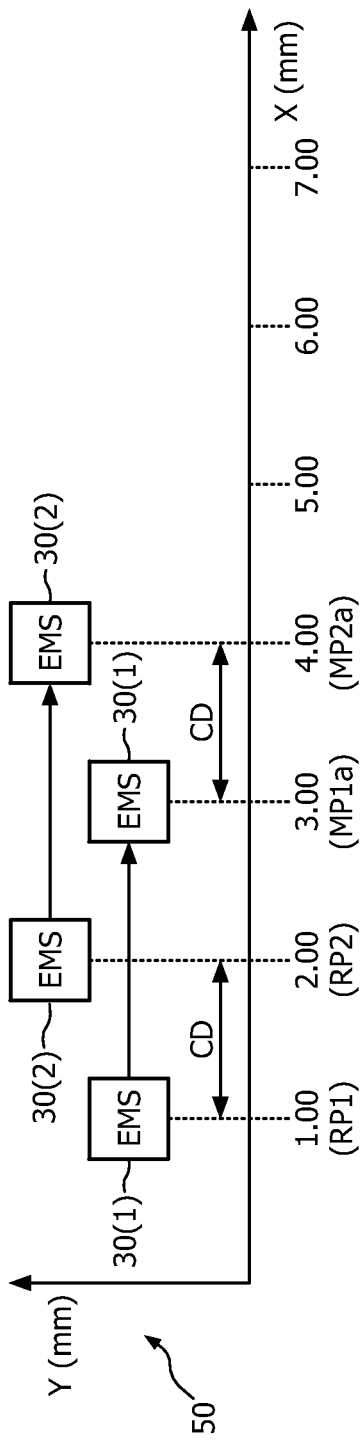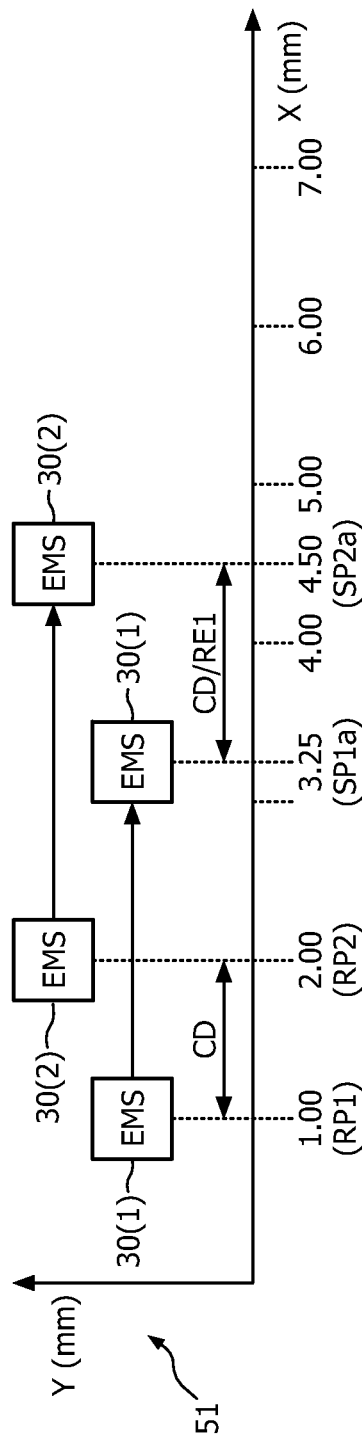
FIG. 2A Prior art
FIG. 2B Prior art

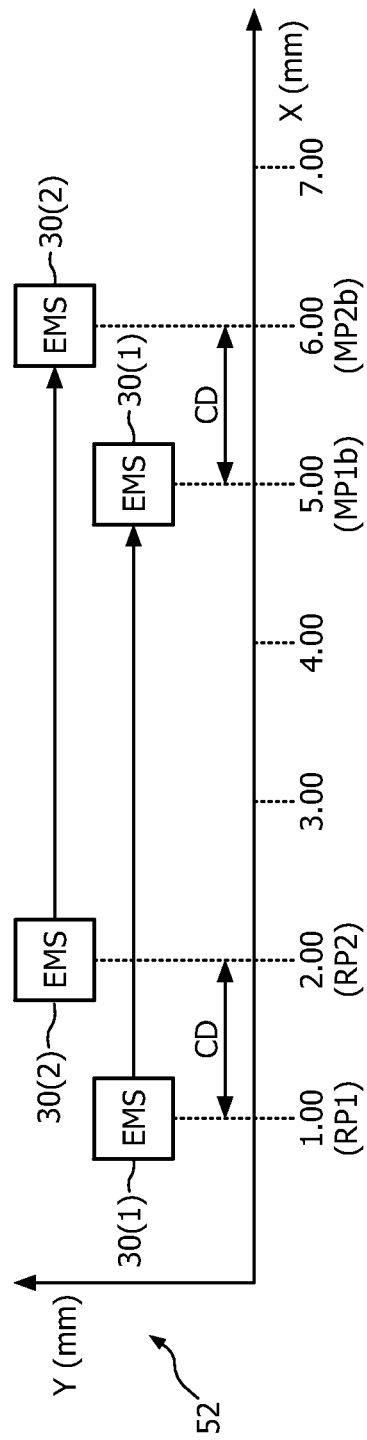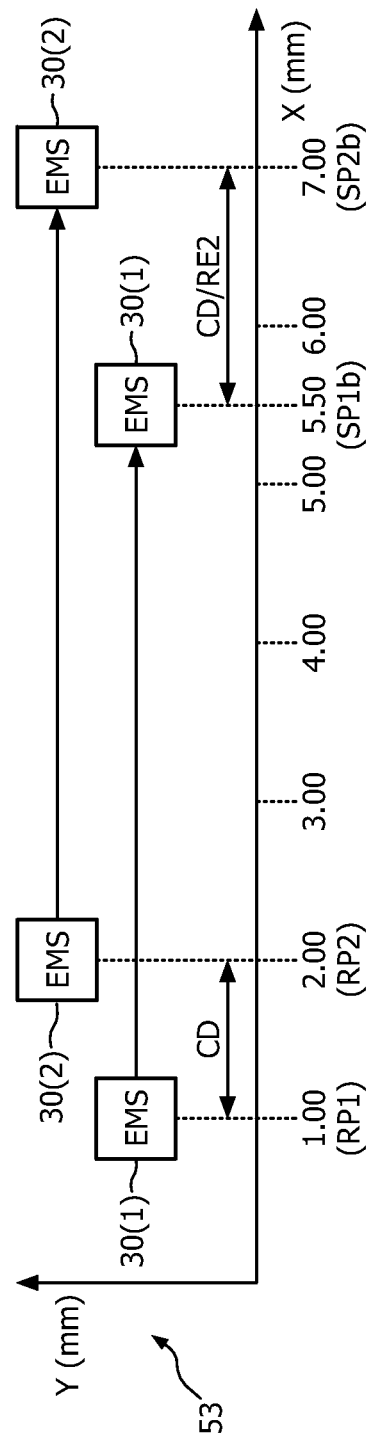
FIG. 3A Prior art
FIG. 3B Prior art

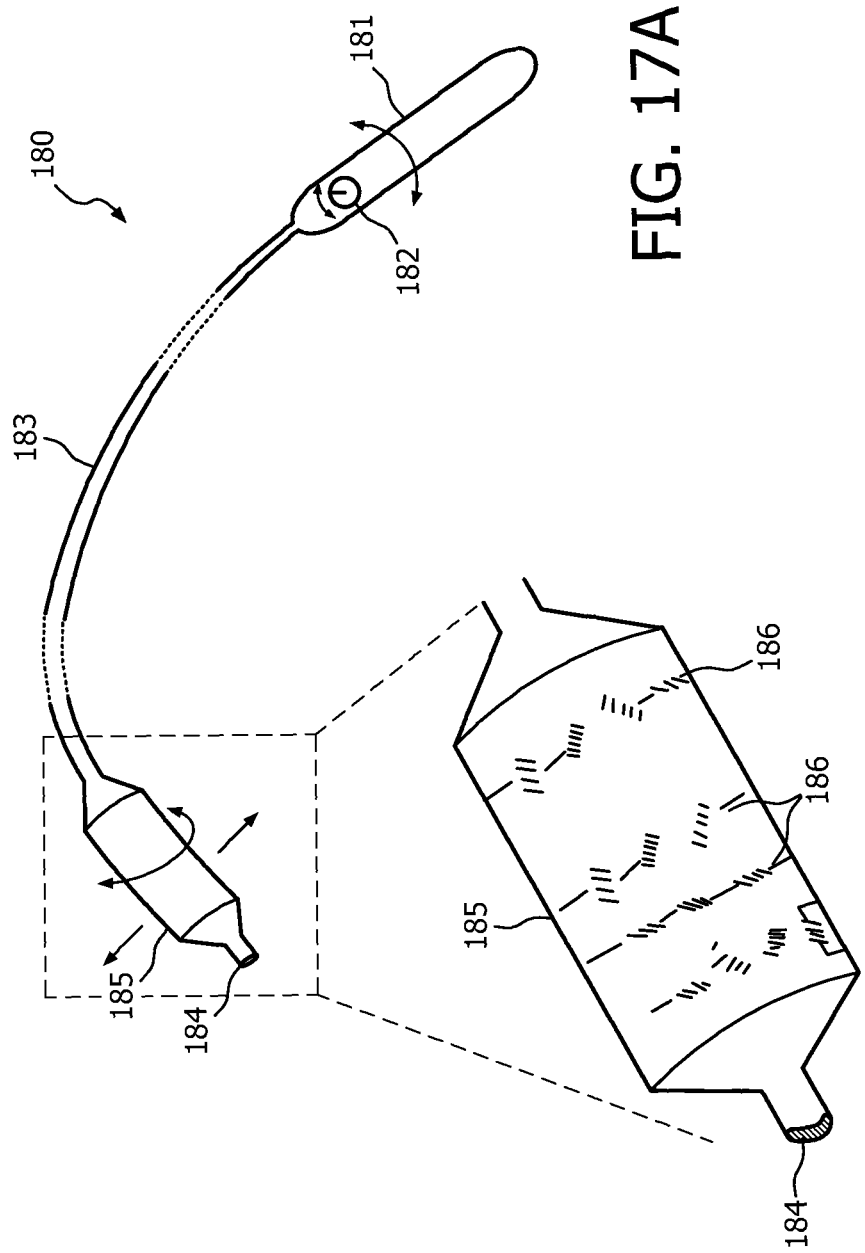

METHOD AND SYSTEM FOR CHARACTERIZING AND VISUALIZING ELECTROMAGNETIC TRACKING ERRORS

The present invention generally relates to electromagnetic tracking systems for clinical procedures. The present invention specifically relates to a characterization and a visualization of electromagnetic tracking errors within electromagnetic fields.

Electromagnetic tracking systems are often used for real time navigation of surgical tools in an Image Guided Therapy ("IGT") system. Electromagnetic tracking systems are however very sensitive to electromagnetic field distortions. These distortions arise in a clinical environment due to a presence of a ferromagnetic interventional apparatus or other metallic medical equipment. In the presence of a field distortion, electromagnetic tracking measurements result in non-uniform, complex error distributions that impact the ability of a physician to navigate the surgical tools for therapy delivery with accuracy and precision.

The ability to rapidly characterize and map any potential errors in the interventional workspace plays an important role in providing physicians with information about whether the desired location of treatment can be targeted with confidence. Thus, attempts have been made to characterize and correct electromagnetic tracking errors based on pre-procedural calibration techniques. For example, a pre-operative static map of the whole electromagnetic field may be generated for use as a look-up table to correct electromagnetic tracking errors at any given position/orientation of each electromagnetic sensor. By further example, optical markers exclusively or in conjunction with electromagnetic sensors may be used. However, clinical environments dynamically change during a procedure making pre-procedural calibration measurements difficult to apply intra-procedurally.

The present invention detects and characterizes electromagnetic tracking errors by mapping absolute and relative errors pre-procedurally within an electromagnetic field. To this end, a calibration tool or a surgical tool includes an electromagnetic sensor array of two or more electromagnetic sensors in a known geometrical configuration. This approach is distinct from other calibration tool designs in that error characterization is derived solely from electromagnetic sensor measurements rather than by using reference measurements from optical markers or other sensing techniques. The relative error is measured as the difference between the known geometry and the electromagnetically sensed one in real time. Using statistical mapping, a desired absolute error field space is measured either in the clinic as the part of daily quality control checks, or before the patient comes in, or in vivo. A resulting error field displayed to the physician provides clear visual feedback about measurement confidence or reliability of localization estimates of the absolute errors in electromagnetic tracking.

One form of the present invention is an electromagnetic error tracking method having a calibration stage, a pre-operative stage and an intra-operative stage. For purposes of the present invention, the term "calibration" as used herein is broadly defined to describe any activity occurring or related to a calibration of an electromagnetic sensor array, the term "pre-operative" as used herein is broadly defined to describe any activity occurring or related an application of calibration data of the electromagnetic sensor for purposes of generating an error map as further described herein, and the term "intra-operative" as used herein is broadly defined to describe any activity occurring or related to an application of the pre-operative error map for purposes of generating an absolute error field as further described herein.

The calibration stage involves a design of a calibration/surgical tool having a known geometrical configuration of an electromagnetic sensor array of two (2) or more electromagnetic sensors (e.g., coils). The electromagnetic sensor array is disposed within a calibration electromagnetic field, and a calibrated distance between one or more electromagnetic sensors pairs is measured from a sensing of the electromagnetic sensor array within the calibration electromagnetic field. For purposes of the present invention, the term "electromagnetic sensor pair" is broadly defined herein as any two (2) electromagnetic sensors of the electromagnetic sensor array designated as a pair for purposes of calibrating the electromagnetic sensor array and for computing relative errors as further described herein.

The pre-operative stage involves a controlled movement of the electromagnetic sensor array within a pre-operative electromagnetic field between numerous measurement positions. For each electromagnetic sensor, a pre-operative absolute error for the electromagnetic sensor is measured at each measurement position of the electromagnetic sensor with the each pre-operative absolute error for the electromagnetic sensor being an absolute differential between a measurement position and a sensed position of the electromagnetic sensor within the pre-operative electromagnetic field. Also for each electromagnetic sensor pair, a pre-operative relative error is measured at each measurement position with each pre-operative relative error being an absolute differential between a calibrated distance between the electromagnetic sensor pair and a sensed distance between the electromagnetic sensor pair within the pre-operative electromagnetic field. A pre-operative error map is generated from a statistical relationship between the pre-operative absolute errors and the pre-operative relative errors.

The intra-operative stage involves a controlled movement of the electromagnetic sensor array within an intra-operative electromagnetic field between numerous estimation positions. For each electromagnetic sensor pair, an intra-operative relative error is measured at each estimation position with each intra-operative relative error being an absolute differential between a calibrated distance between an electromagnetic sensor pair and a sensed distance between the electromagnetic sensor pair within the intra-operative electromagnetic field. For each estimation position, an intra-operative absolute error is estimated from a plotting of the corresponding intra-operative relative error within the pre-operative error map of the pre-operative absolute errors and the pre-operative relative errors. The intra-operative stage may further involve feedback (e.g., visual, audio and/or tactile) representative of the estimated intra-operative absolute errors. In one embodiment, an image of an object within the intra-operative electromagnetic field (e.g., an anatomical region of a body) may be integrated with a visual feedback of an intra-operative absolute error field having one or more reliable zones indicative of one or more undistorted areas in the intra-operative electromagnetic field and/or one or more unreliable zones indicative of one or more distorted areas in the intra-operative electromagnetic field. The intra-operative absolute error field may be derived from a comparison of the estimated intra-operative absolute errors to a reliability threshold.

A second form of the present invention is an electromagnetic tracking system of the present invention employing a tool (e.g., calibration or surgical) including the electromagnetic sensor array and a data processor for executing one or more of the calibration stage, the pre-operative stage and the intra-operative stage.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

FIGS. 2A and 3A illustrate exemplary translations of two (2) electromagnetic sensors along an X-axis as known in the art.

FIGS. 2B and 3B illustrate an exemplary distorted electromagnetic tracking of two (2) electromagnetic sensors shown in FIGS. 2A and 3A as known in the art.

FIGS. 15-18 illustrate exemplary embodiments of electromagnetic tracking catheters in accordance with the present invention.

Figure 1:
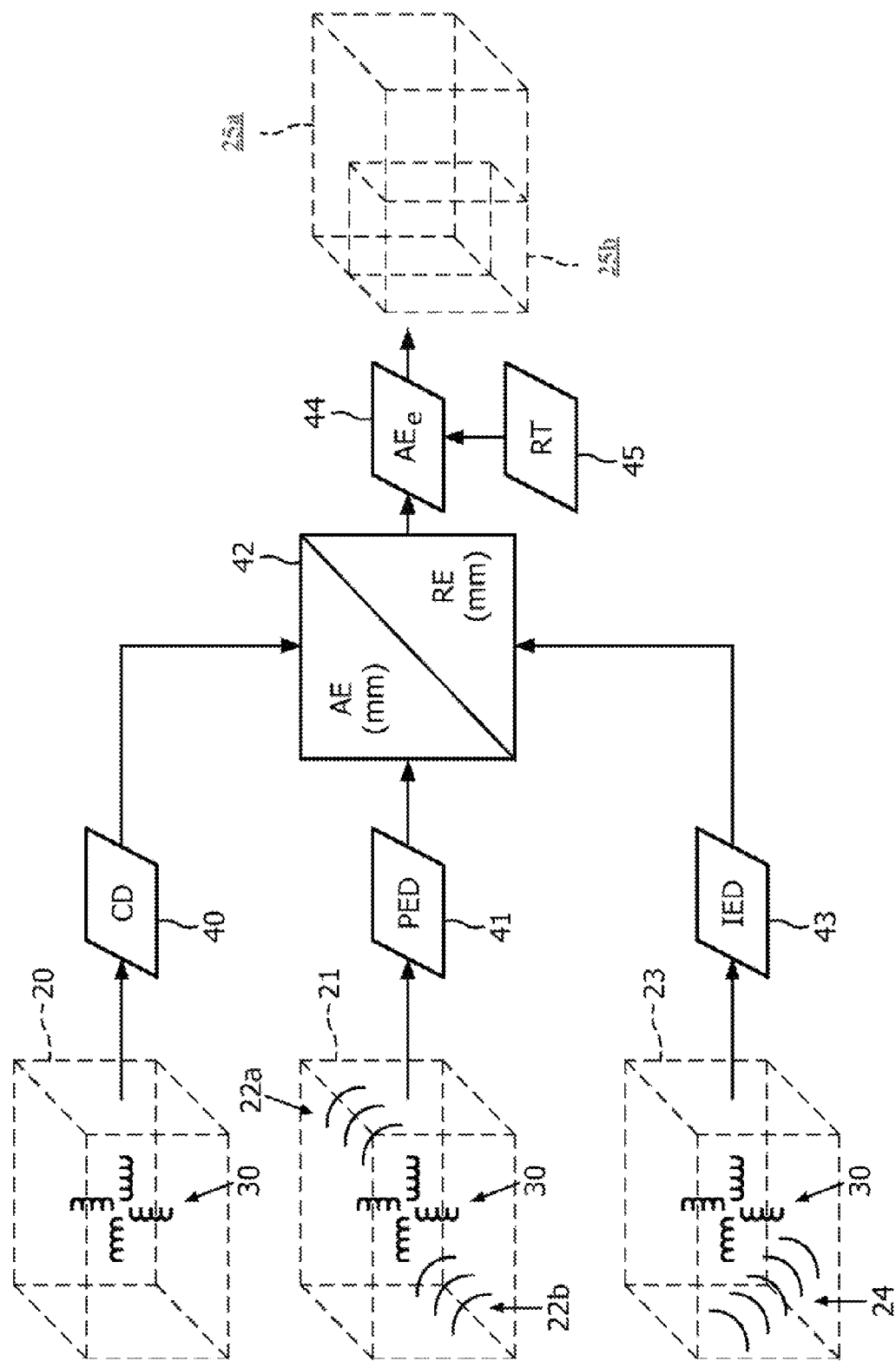
FIG. 1 illustrates an exemplary embodiment of a characterization and visualization of electromagnetic errors tracked within electromagnetic fields in accordance with the present invention.

One definition of an absolute error for an electromagnetic sensor as known in the art is a registration error between a tracking of an electromagnetic sensor and a reference navigation system (e.g., a robot or an optical tracking system.) The present invention is premised on a measurement of relative errors between two (2) electromagnetic sensors having correlated absolute errors. FIGS. 1-3 illustrate an exemplary measurement of relative errors to facilitate an understanding of the concept of relative errors in accordance with the present invention.

Specifically, FIG. 1 illustrates a spatial volume 20 enclosing an undistorted calibration electromagnetic field (not shown for clarity purposes), a spatial volume 21 enclosing a distorted pre-operative electromagnetic field (not shown for clarity purposes) as evidenced by the electromagnetic waves 22a and 22b, and a spatial volume 23 enclosing a distorted intra-operative electromagnetic field (not shown for clarity purposes) as evidenced by the electromagnetic waves 24.

For spatial volume 20, an electromagnetic sensor array 30 (e.g., coils) having a known geometrical configuration is disposed within the calibration electromagnetic field that is generated in a clean room. A sensing of the coils facilitates a measurement of a calibrated distance between pairs of electromagnetic sensors. For example, FIG. 2A illustrates a calibrated distance CD of 1 mm between a pair of electromagnetic sensors 30(1) and 30(2). A dataset 40 of calibration measurements for all measured calibrated distances is generated for computing relative errors as will be further described herein. In practice, a calibrated distance is preferably measured for each distinct pairing of electromagnetic sensors (e.g., twenty-eight (28) pairs exist for six (6) electromagnetic sensors).

Referring back to FIG. 1, for spatial volume 21, electromagnetic sensor array 30 is disposed within the pre-operative electromagnetic field that is generated in a clinical environment having ferromagnetic interventional equipment or other metallic medical equipment (e.g., a computer tomography system). For each electromagnetic sensor, a pre-operative absolute error is measured as the electromagnetic sensor array 30 is moved within the pre-operative electromagnetic field. In addition, for each electromagnetic sensor pair, a pre-operative relative error is measured.

For example, FIG. 2A illustrates two electromagnetic sensors 30(1) and 30(2) having a calibrated distance of 1 mm at respective reference positions RP1 and RP2 external to the pre-operative electromagnetic field 21, and a two (2) mm controlled movement 50 of electromagnetic sensors 30(1) and 30(2) from respective reference positions RP1 and RP2 along an X-axis to respective measurement positions MP1a and MP2a within the pre-operative electromagnetic field. Due to distortions 22a and 22b within the pre-operative electromagnetic field 21, electromagnetic sensors 30(1) and 30(2) are tracked as being moved to respective sensed positions SP1a and SP2a as shown in FIG. 2B. A pre-operative absolute error AE1a for electromagnetic sensor 30(1) is the absolute differential between measurement position MP1a and sensed position SP1a, which is 0.25 mm. A pre-operative absolute error AE2a for electromagnetic sensor 30(2) is an absolute differential between measurement position MP2a and sensed position SP2a, which is 0.50 mm. Thus, a pre-operative relative error RE1 is the absolute differential between pre-operative absolute errors AE1a and AE1b, which is 0.25 mm. More particularly, pre-operative relative error RE1 is an absolute differential between calibrated distance CD of electromagnetic sensors 30(1) and 30(2) of 1.00 mm and a sensed distance between electromagnetic sensors 30(1) and 30(2) of 1.25 mm, which is 0.25 mm.

FIG. 3A illustrates an additional (2) mm controlled movement 52 of electromagnetic sensors 30(1) and 30(2) from respective measurement positions MP1a and MP2a along an X-axis to respective measurement positions MP1b and MP2b within the pre-operative electromagnetic field 21. Again, due to distortions 22a and 22b with the pre-operative electromagnetic field, electromagnetic sensors 30(1) and 30(2) are tracked as being moved to respective sensed positions SP1b and SP2b as shown in FIG. 3B. A pre-operative absolute error AE1b for electromagnetic sensor 30(1) is the absolute differential between measured position MP1b and sensed position SP1b, which is 0.50 mm. A pre-operative absolute error AE2b for electromagnetic sensor 30(2) is the absolute differential between measured position MP2b and sensed position SP2b, which is 1.00 mm. Thus, a pre-operative relative error RE2 is the absolute differential between pre-operative absolute errors AE2a and AE2b, which is 0.50 mm. More particularly, pre-operative relative error RE2 is an absolute differential between calibrated distance CD of electromagnetic sensors 30(1) and 30(2) of 1 mm and a sensed distance between electromagnetic sensors 30(1) and 30(2) of 1.50 mm, which is 0.50 mm.

Referring back to FIG. 1, a dataset 41 including the measured pre-operative absolute errors and the measured pre-operative relative errors is used to generate a pre-operative error map 42 derived from a statistical relationship between the pre-operative errors as will be further described herein.

For the spatial volume 23, electromagnetic sensor array 30 is disposed within the intra-operative electromagnetic field that is generated in a clinical environment having ferromagnetic interventional equipment or other metallic medical equipment (e.g., an X-ray system). For each electromagnetic sensor pair, an intra-operative relative error is measured as the electromagnetic sensor array 30 is moved to numerous estimation positions with each intra-operative relative error being an absolute differential between a calibrated distance of the electromagnetic sensor pair and a sensed distance between the electromagnetic sensor pair within the intra-operative electromagnetic field. For each estimation position, an intra-operative absolute error is estimated from a plotting of the corresponding intra-operative relative error within the pre-operative error map 42.

For example, referring to FIGS. 2A and 2B, electromagnetic sensors 30(1) and 30(2) having a calibrated distance of 1 mm at respective reference positions RP1 and RP2 external to the intra-operative electromagnetic field 21 may experience an intra-operative relative error of 0.25 mm when electromagnetic sensors 30(1) and 30(2) are moved two (2) mm respective reference positions RP1 and RP2 along an X-axis to respective measurement positions MP1a and MP2a within the intra-operative electromagnetic field. A plotting of the intra-operative relative error of 0.25 mm (e.g., relative error RE1 shown in FIG. 2B) within pre-operative error map 42 results in an estimation of an intra-operative absolute error as a function of 0.25 mm and 0.50 mm (e.g., absolute errors AE1 and AE2 of FIG. 2B) in dependence on the statistical relationship of the errors in map 42.

By further example, as shown in FIG. 3A, electromagnetic sensors 30(1) and 30(2) may experience an intra-operative relative error of 0.50 mm when electromagnetic sensors 30(1) and 30(2) are further moved from respective measurement positions MP1a and MP2a along an X-axis to respective measurement positions MP1b and MP2b within the intra-operative electromagnetic field. A plotting of an intra-operative relative error of 0.50 mm (e.g., relative error RE2 shown in FIG. 3B) within pre-operative error map 42 results in an estimation of an intra-operative absolute error as a function of 0.5 mm and 1.0 mm (e.g., absolute errors AE1 and AE2 of FIG. 3B) in dependence on the statistical relationship of the errors in map 42.

A dataset 44 of estimated intra-operative absolute errors is used to generate feedback (e.g., visual, audio and/or tactile) representative of the estimated intra-operative absolute errors. As shown in FIG. 1, the feedback may take the form of an intra-operative absolute error field 25 having a reliable zones 25a indicative of an undistorted area in the intra-operative electromagnetic field (i.e., an absence of distortion in an area of spatial volume 23) and an unreliable zone 25b indicative of the distorted area in the intra-operative electromagnetic field (i.e., a presence of a distortion 24 in an area of spatial volume 23). The feedback, in particular, intra-operative absolute error field 25, may be derived from a comparison of the estimated intra-operative absolute errors to a reliability threshold 45.

Various embodiments of the present invention will now be described herein in connection with FIGS. 4-19.

Figure 4:
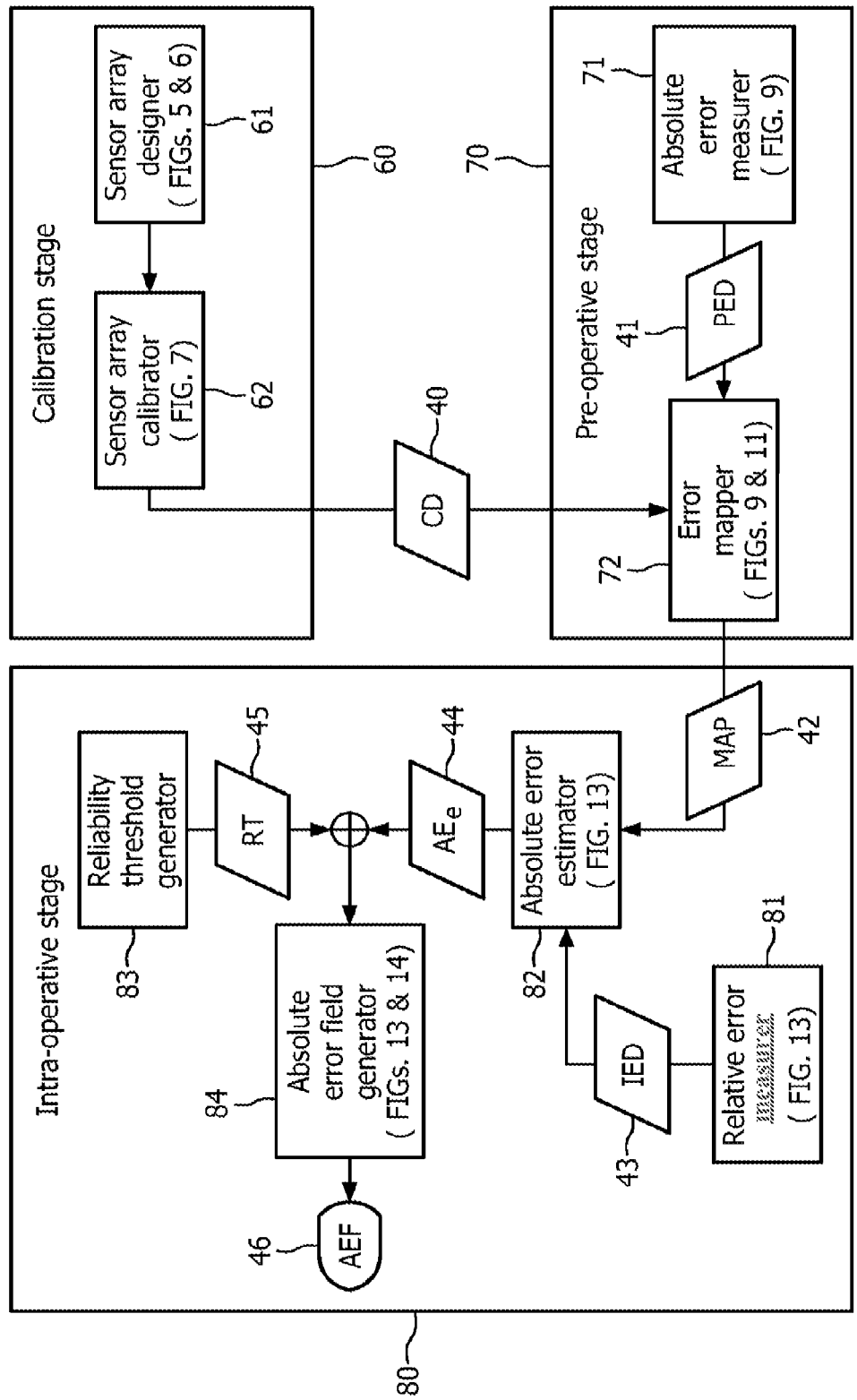
FIG. 4 illustrates an exemplary embodiment of a block diagram of an electromagnetic tracking method in accordance with the present invention.

FIG. 4 illustrates a calibration stage 60, a pre-operative stage 70 and an intra-operative stage 80.

Figure 5:
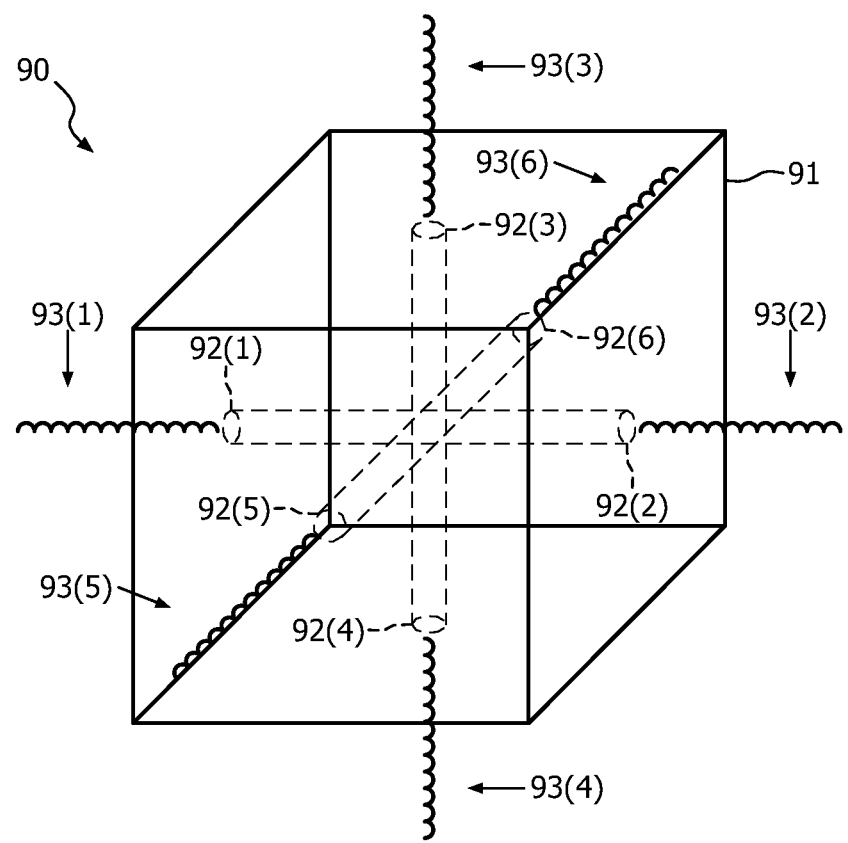
FIG. 5 illustrates an exemplary embodiment of a schematic diagram of a calibration tool in accordance with the present invention.
Figure 6:
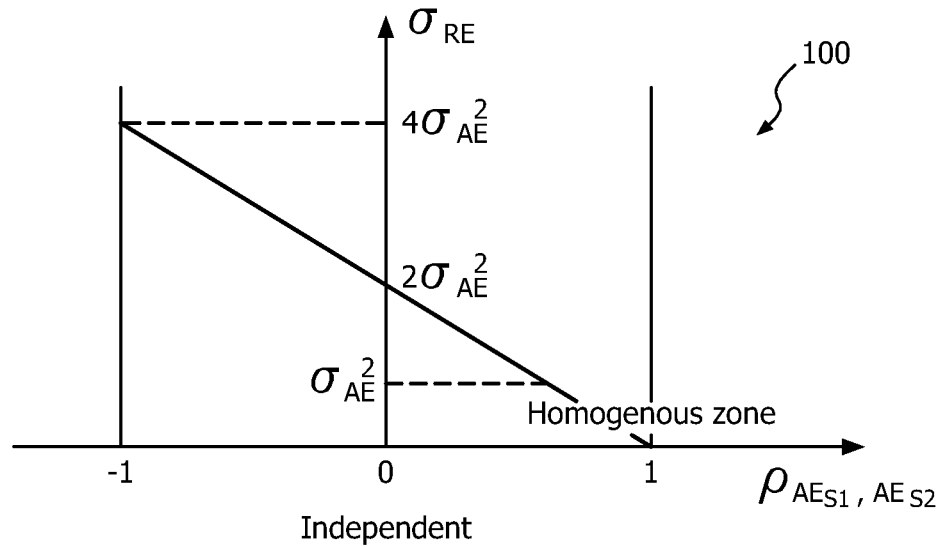
FIG. 6 illustrates an exemplary correlation graph of absolute errors in accordance with the present invention.

Calibration stage 60 includes a sensor array designer 61 for defining a geometrical configuration of electromagnetic sensors for a calibration tool or a surgical tool. In practice, the geometrical configuration may have any positioning and orientation of each electromagnetic sensor suitable within the array for tracking the electromagnetic sensors in a clinical environment. In one exemplary embodiment as shown in FIG. 5, a calibration tool 90 includes a non-magnetic cubical body 91 (e.g., plastic) having a geometrical configuration of six (6) electromagnetic sensors 93 within six (6) axial channels 92. A handle (not shown) may be coupled to one of the sides of body 91 whereby tool 90 may be operated as a wand. In the wand side, the electromagnetic sensor associated with the side of body 91 coupled to the handle may be omitted.

In order to establish, a statistical relation between relative errors and absolute errors as will be further explained herein, the electromagnetic measurements from electromagnetic sensor pair 93(1) and 93(2) for example may be considered as two random variables. As such, the relative error between electromagnetic sensor pair 93(1) and 93(2) is the difference between two random variables AES1 and AES2, which are the errors in world coordinates, which are referred to as absolute errors at electromagnetic sensors 93(1) and 93(2) respectively. Assuming that the probability density functions for absolute errors AES1 and AES2 are identically distributed with zero means in accordance with the follow equation:

$$E[RE]=\mu_{RE}=E[AE_{S1}]-E[AE_{S2}]=0$$

In addition, the variances $\sigma_{RE}^2=E[(RE-\mu\_RE)^2]=2\sigma_{AE_{S1}}^2(1-\rho(AE_{S1},AE_{S2}))$, where $\sigma_{AE_{S1}}$ and $\rho(AE_{S1}, AE_{S2})$ are the standard deviation of AES1 and correlation factor between AES1 and AES2, respectively. Whenever the sensors 93(1) and 93(2) are physically close to each other, they are highly linearly correlated in the positive direction, thereby driving down the variability in relative error RE,$\sigma_{RE}$, to zero and making the relative error RE homogenous.

For the present invention, the smaller variability of relative error RE is used to estimate the value of absolute tracking AE. In order for degree of variation to be minimal, the above equation [1] imposes two conditions. First, the two sensors 93(1) and 93(2) should not be far apart from each other, and second, the distance of the sensors 93(1) and 93(2) from electromagnetic field generator (not shown) should not be large. If the first condition is violated, then the correlation coefficient will not be close to one (1), thereby increasing the variation in consecutive relative error RE measurements. If the second condition is violated, $\sigma_{AE_{S1}}^2$ will be high, in turn increasing the variance of relative error RE. The relationship between these three variables—$\sigma_{AE_{S1}}^2$, $\rho$, and $\sigma_{RE}^2$ is shown in the correlation graph 100 of FIG. 6.

Figure 7:
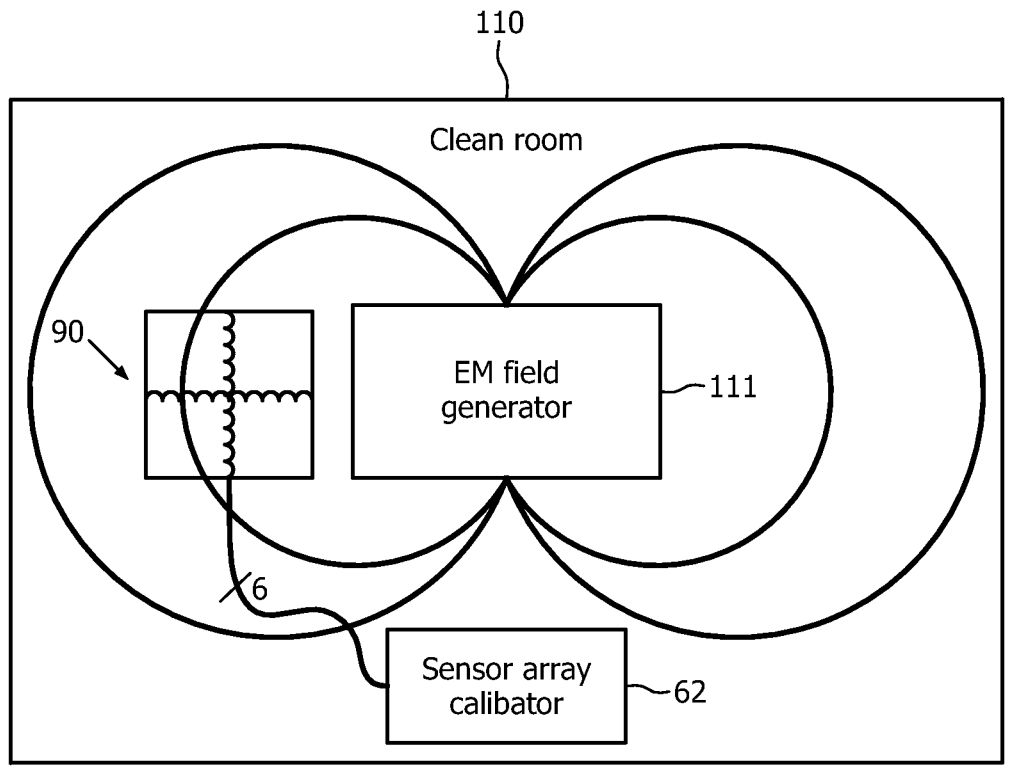
FIG. 7 illustrates an exemplary calibration of the calibration tool shown in FIG. 5 in accordance with the present invention.

Calibration stage 60 further includes a sensor array calibrator 62 for measuring a calibration distance CD between pairs of electromagnetic sensors. For example, as shown in FIG. 7, an electromagnetic field generator 111 is employed in a clean room 1000 (e.g., zero electromagnetic distortions) whereby the electromagnetic field generated by generator 111 facilitates a detection of a position and orientation of each electromagnetic sensor 93 and a measurement of a calibration distance between pairs of electromagnetic sensors 93 (e.g., a calibration distance between electromagnetic sensor 93(1) of FIG. 5 and one or more of the remaining five (5) electromagnetic sensors 93, etc.).

Pre-operative stage 70 employs an absolute error measurer 71 for measuring pre-operative absolute errors and computing pre-operative relative errors as previously described herein for FIGS. 1-4. In one exemplary embodiment, the calibration/surgical tool is moved in a controlled manner within a pre-operative electromagnetic field to numerous measurement positions. At each measured position, absolute error measurer 71 measures an absolute error for each electromagnetic sensor with the absolute error for each electromagnetic sensor being an absolute differential between the measured position and a sensed position of the electromagnetic sensor. Also at each measurement position, absolute error measurer 71 computes a pre-operative relative error for an electromagnetic sensor pair with each pre-operative relative error being an absolute differential between absolute errors of the electromagnetic sensor pair, or more particularly, an absolute differential between the calibrated distance and the sensed distance between the electromagnetic sensor pair.

Pre-operative stage 70 further employs an error mapper 72 for mapping the pre-operative absolute errors and the pre-operative relative errors for each position. The error mapping may be a derived from a statistical relationship between the pre-operative absolute errors and the pre-operative relative errors.

In one exemplary embodiment, each relative error RE may be mapped to a probable absolute error observation AE at a given measurement location. Given a specific value of relative error RE, the minimum mean square error estimator of absolute error AE is the expected value of the conditional probability, $\widehat{AE} = E[AE|RE] = \int (ae) f(AE|RE) d(ae)$ where f is the conditional probability density function of absolute error AE given relative error RE. Therefore, if the joint probability fimcdori of absolute error AE and relative error RE is empirically estimated, then the statistics of the absolute errors AE can be estimated using the relative errors RE. This can be done by collecting large samples of data and observing the relationship between absolute and relative errors.

Figure 10:
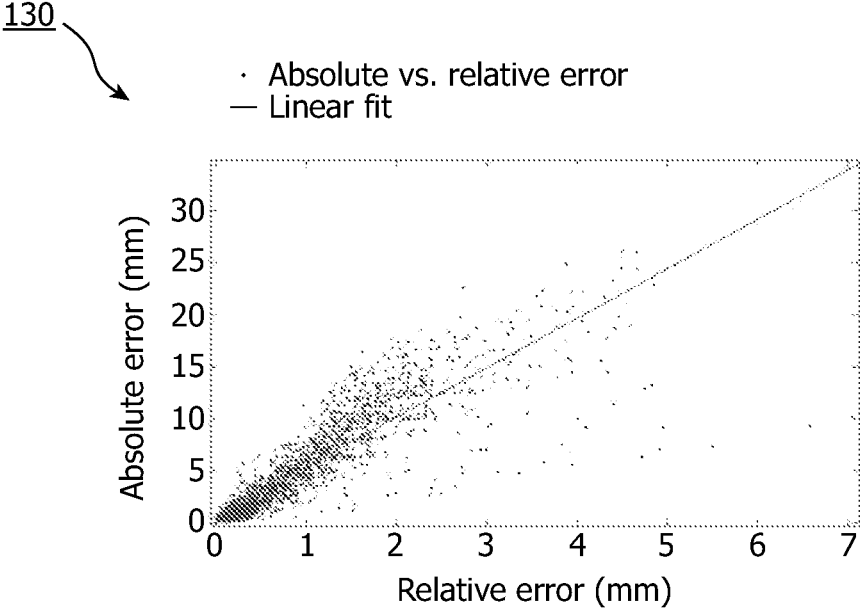
FIG. 10 illustrates an exemplary pre-operative error map in accordance with the present invention.
Figure 11:
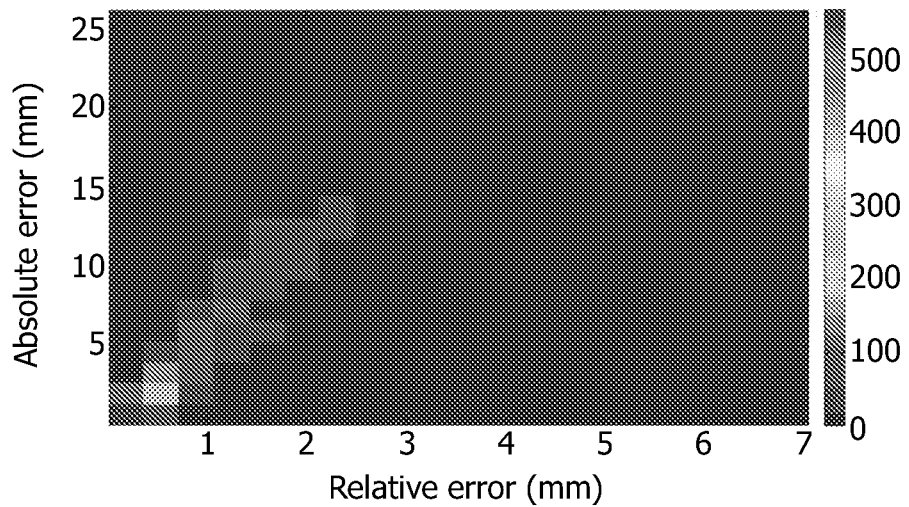
FIG. 11 illustrates an exemplary 2D histogram in accordance with the present invention.
Figure 13:
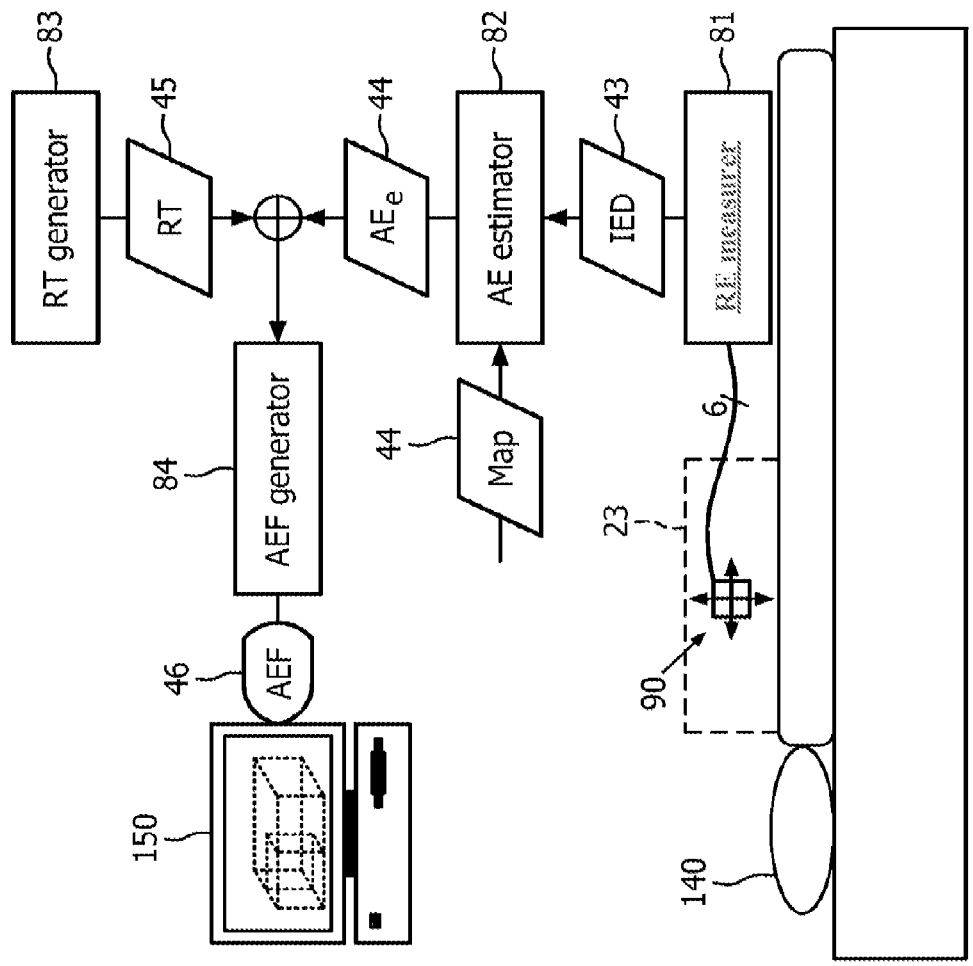
FIGS. 12 and 13 illustrate respective top and side views of an exemplary intra-operative absolute error estimations and intra-operative absolute error field generations in accordance with the present invention.
Figure 12:
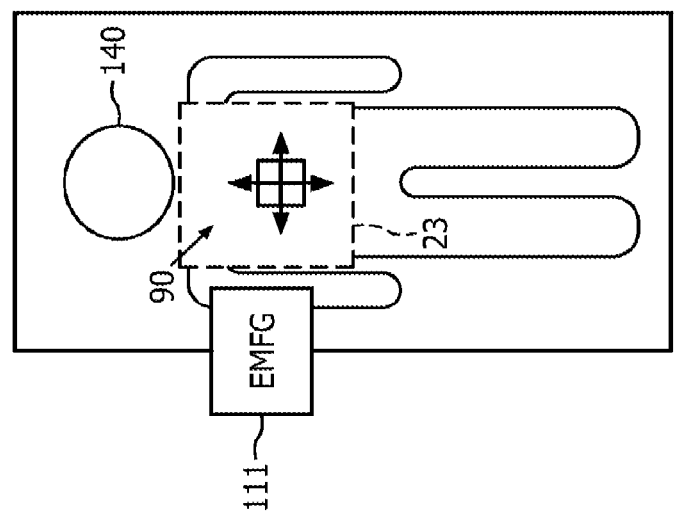

In estimating the joint probability, it is important to make sure that the measurements are made under different types of expected/realistic electromagnetic distorted environments. In one embodiment, data is collected from both highly distorted and minimally distorted environments in vicinity of an X-ray gantry or CT scanner. Six (6) sets of data is collected, each dataset including more than 13,000 points. Within each dataset, absolute errors are measured. The union of the six (6) datasets is normalized to get a probability mapping of absolute error AE versus relative error RE. FIG. 10 illustrates a mapping 130 in a distorted electromagnetic environment. FIG. 10 shows the mapping 130 between absolute error AE and relative error RE for one sensor's measurement. A linear fit through the data shows the necessary linear correlation between the two variables. A corresponding 2D histogram 131 with the relative error RE in the x-axis and absolute error AE in the y-axis is shown in FIG. 11. A final 2D histogram is a union of all such histograms from different environments with varying degrees of electromagnetic distortions in the workspace. The generation of the final 2D histogram can be performed periodically as a tracking error characterization/calibration of the interventional workspace within an interventional setting.

Figure 9:
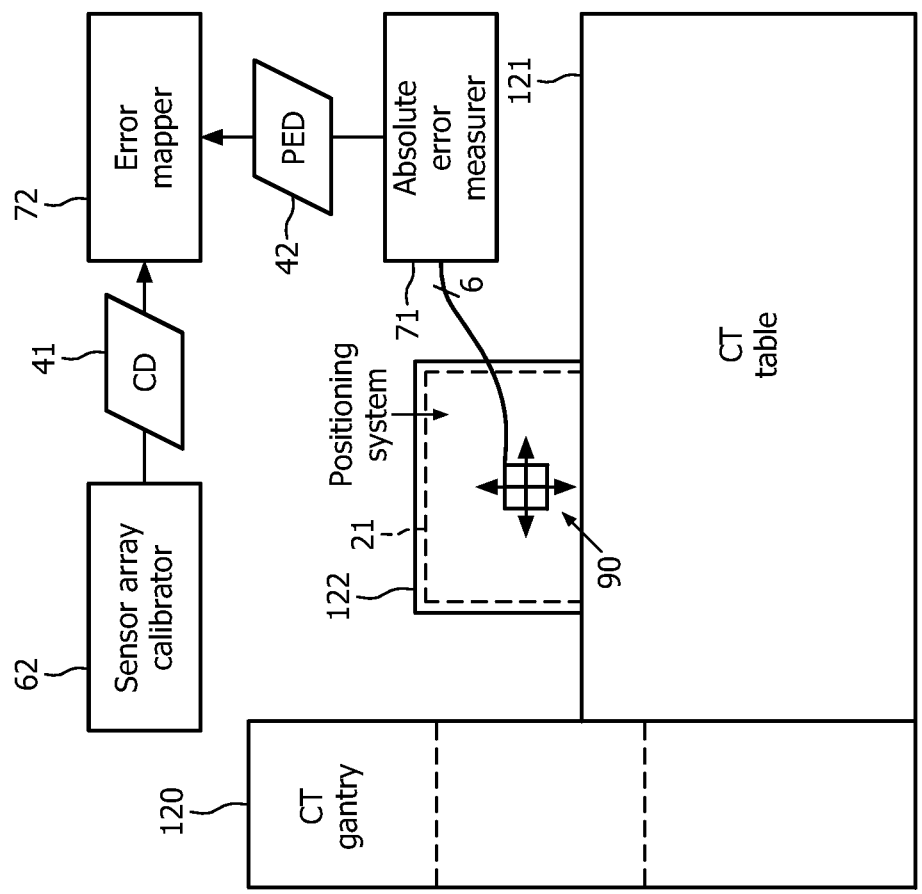
FIGS. 8 and 9 illustrate respective front and side views of an exemplary pre-operative absolute error/relative error measurements and pre-operative error mapping in accordance with the present invention.
Figure 8:
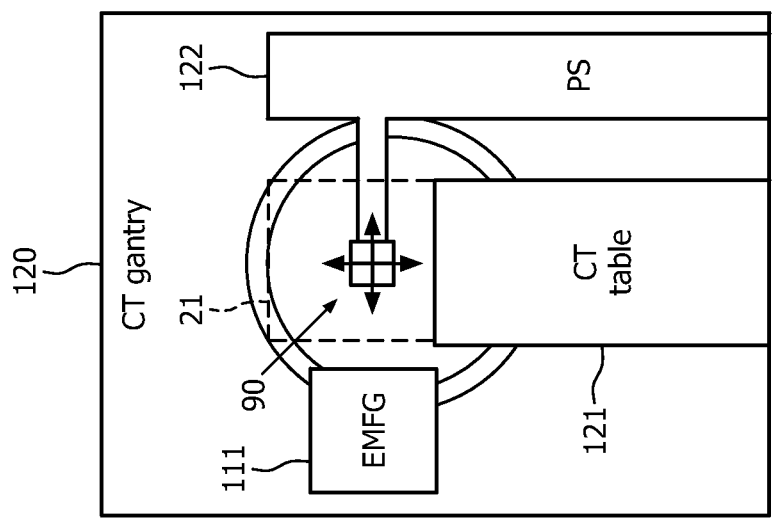

In practice, pre-operative stage 70 may be run within any clinical environment having electromagnetic distortions. For example, as shown in FIGS. 8 and 9, calibration tool 90 is moved in a controlled manner by a positioning system 122 (e.g., a robot or optical tracker) through an electromagnetic field (not shown) generated by an electromagnetic generator 111 relative to a CT gantry 120 and a CT table 121. The CT gantry 120 distorts the electromagnetic field causing absolute errors for calibration tool 90. Absolute error measurer 71 measures an absolute error for each electromagnetic sensor with the absolute error for each electromagnetic sensor being an absolute differential between a measurement position and a sensed position of the electromagnetic sensor. Also at each position, absolute error measurer 71 computes a pre-operative relative error for each electromagnetic sensor pair with each pre-operative relative error being an absolute differential between absolute errors of the electromagnetic sensor pair, or more or more particularly, an absolute differential between the calibrated distance and the sensed distance between the electromagnetic sensor pair. Responsive to pre-operative error dataset 42 from absolute error measurer 71 and the calibration measurement dataset 40 from sensor array calibrator 62, error mapper 72 ma
the pre-operative absolute errors and the pre-operative relative errors for each position.

Referring again to FIG. 4, intra-operative stage 80 employs a real-time error measurer 81 for measuring intra-operative relative errors 43 for electromagnetic sensor pairs at each estimation position, and an absolute error estimator 82 estimates intra-operative absolute errors 44 for each electromagnetic sensor at each estimation position. The estimation of the intra-operative absolute errors is derived from a plotting of the intra-operative relative errors within the pre-operative error map 42. Intra-operative stage 60 further employs a reliability threshold generator 83 and an absolute error field generator 84 for generating feedback (e.g., visual, audio and/or tactile) in the form of an intra-operative absolute error field derived from a comparison of the estimated absolute errors 44 to a reliability threshold 45 (e.g., 2 mm). Specifically, any intra-operative absolute error below the reliability threshold 45 is deemed as being reliable for accurate tracking despite any distortion within the corresponding area of the intra-operative electromagnetic field. Conversely, any intra-operative absolute error above the reliability threshold 45 is deemed as being unreliable for accurate tracking within a corresponding area of the intra-operative electromagnetic field.

In one exemplary embodiment, an estimate of absolute error AE for the workspace can be measured by taking relative error RE measurements at N different locations in the workspace. For each location, an estimate of absolute error AE can be measured using the 2D histogram by executing the following steps. The first step involves a measurement of the marginal pdf of P(RE) by summing along the rows of the 2D histogram and normalizing. The second step, for each measurement of relative error RE, involves a consideration of a corresponding column of the histogram and a weighing of the probability values of that column by 1/P(RE) to get probability distribution P(AE|RE). The third step involves a measurement of E(AE|RE) by computing the mean of this conditional probability distribution. The fourth step involves a repeating of the first three (3) steps for N different measurements of relative error RE, and the mean (E(AE|RE) is measured. This mean reflects the estimated value of AE given N different RE measurements. The fifth step involves a measurement of a standard deviation, $\sigma_{AE|RE}$, from N measurements of relative error RE to get an estimate of confidence in the estimation of absolute error AE. For each set of N measurements, the result from the fourth step may be used to create an intra-operative absolute error field displayed to the physician as a part of this invention to provide a clear visual feedback about the measurement confidence. In addition, the result from the fifth step provides a confidence of the error estimates.

In practice, intra-operative stage 80 may be run within any clinical environment having electromagnetic distortions. For example, as shown in FIGS, 12 and 13, calibration tool 90 is moved in a controlled manner by a position system (not shown) or medical professional (not shown) through an electromagnetic field (not shown) generated by an electromagnetic field generator 111 relative to an imaging modality (not shown)(e.g., an X-ray machine that distorts the electromagnetic field causing absolute errors for calibration tool 90). A patient 140 as shown may or may not be present. Relative error measurer 81 computes intra-operative relative errors for electromagnetic sensors at each estimation position, and absolute error estimator 82 estimates intra-operative absolute errors derived from a plotting of the intra-operative relative errors within the pre-operative error map 42. Responsive to a comparison of estimated intra-operative absolute errors 44 to reliability threshold 45, absolute error field generator 84 generates a visual feedback in the form of an absolute error field 46 having one or more reliable zones and/or one or more unreliable zones.

Figure 14B:
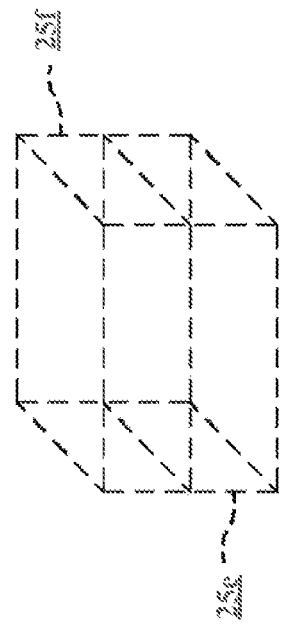
FIGS. 14A-14D illustrate exemplary intra-operative absolute error fields in accordance with the present invention.
Figure 14D:
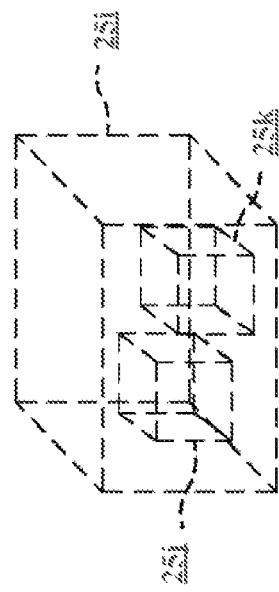
Figure 14A:
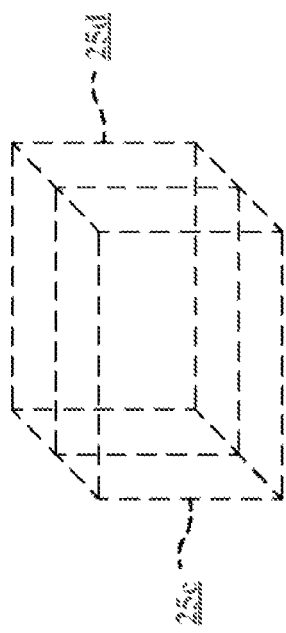
Figure 14C:
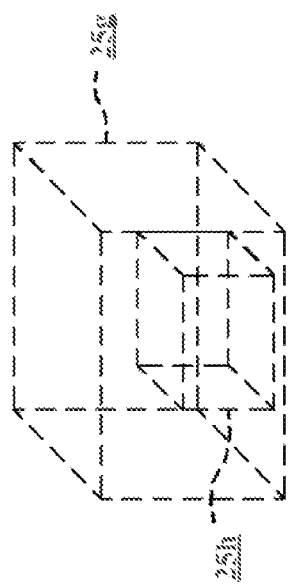

FIGS. 14A-14D illustrate additional exemplary absolute error field. Specifically, FIG. 14A illustrates an exemplary error field having a reliable zone 25c and an unreliable zone 25d side-by-side. FIG. 14B illustrates an exemplary error field having a reliable zone 25e below an unreliable zone 25f. FIG. 14C illustrates an exemplary error field having a reliable zone 25h embedded within an unreliable zone 25g. FIG. 14D illustrates an exemplary error field having reliable zones 25j and 25k embedded within an unreliable zone 25i. The medical professional may use the visualization of the error fields to manipulate a positioning and/or orientation of a patient within the clinical environment in a manner that facilitates an accurate tracking of a surgical tool.

FIGS. 15-18 illustrate surgical tools having a known geometrical configuration of an electromagnetic sensor array for purposes of executing the various stages shown in FIG. 4.

More particularly, an electromagnetic sensor array of a know geometrical configuration may be incorporated into surgical tools (e.g., catheters or needles) for use in detecting reliable zones of operation within an anatomy of interest, such as, for example, an in vivo deployment directly within the tissue of interest. A characterization of EM tracking errors may be performed "live", rather than requiring a separate step immediately prior to patient preparation as with a calibration tool, which streamlines the surgical workflow significantly.

Figures 15A, 15B:
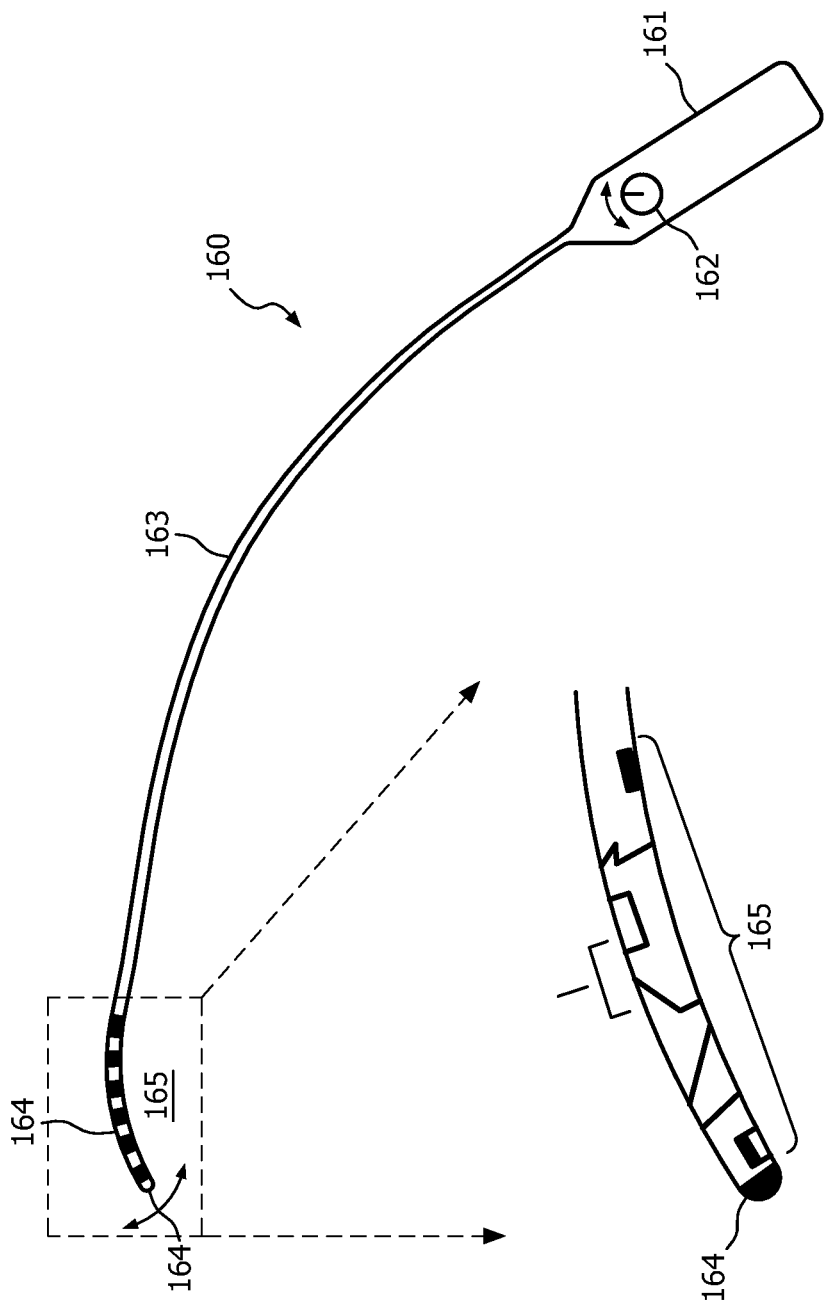

FIG. 15A illustrates a catheter 160 having a handle 161 with a knob 162 at a proximal end and a sheath 163 extending from handle 161 to a distal end having an end effector 164. Adjacent end effector 164 is an electromagnetic sensor array having a plurality of coils 165 as best shown in FIG. 15B. Coils 165 are patterned in a known geometrical configuration on an electronic substrate that is bonded to sheath 163 and covered with a barrier coating (not shown).

Figure 16:
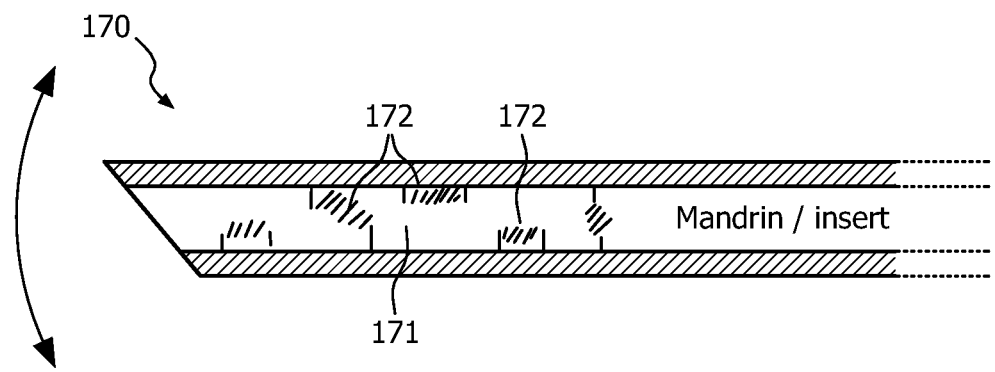

FIG. 16 illustrates a needle/mandrin 170 employing an electromagnetic sensor array having a plurality of coils 172 patterned in a known geometrical configuration on an electronic substrate that is bonded an internal surface of a channel 171 and covered with a barrier coating (not shown).

FIG. 17A illustrates a catheter 180 having a handle 181 with a knob 182 at a proximal end and a sheath 183 extending from handle 181 to a distal end having an end effector 184. Adjacent end effector 184 is a deflectable balloon 185 employing electromagnetic sensor array having a plurality of coils 186 as best shown in FIG. 17B. Coils 186 are patterned in a known geometrical configuration on an electronic substrate that is bonded to sheath 183 and covered with a barrier coating (not shown).

Figure 18:
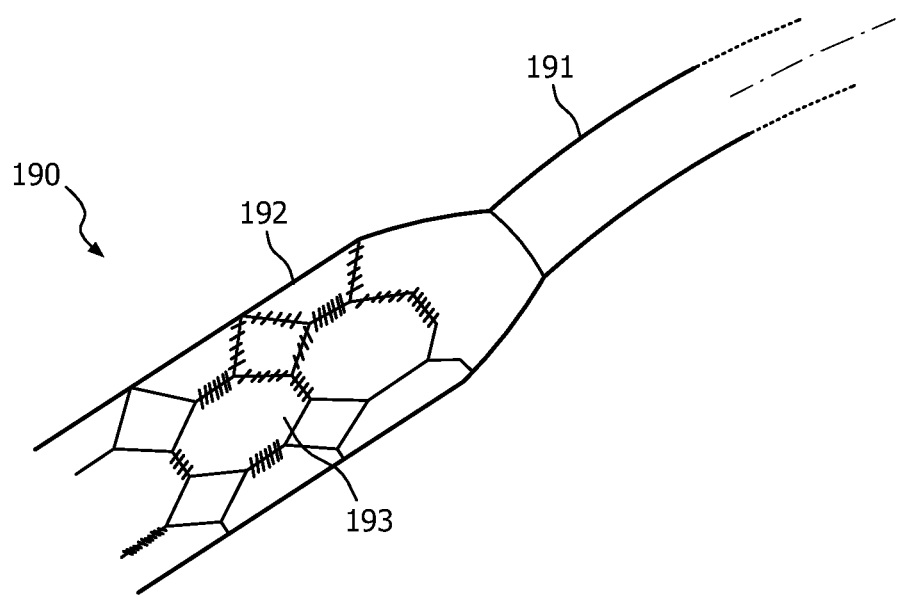

FIG. 18 illustrates a distal end of a catheter 190 having a mesh 192 extending from a sheath 191. Catheter 190 employs electromagnetic sensor array having a plurality of coils 193 patterned in a known geometrical configuration on an electronic substrate that is bonded on mesh 192 and covered with a barrier coating (not shown).

Figure 19:
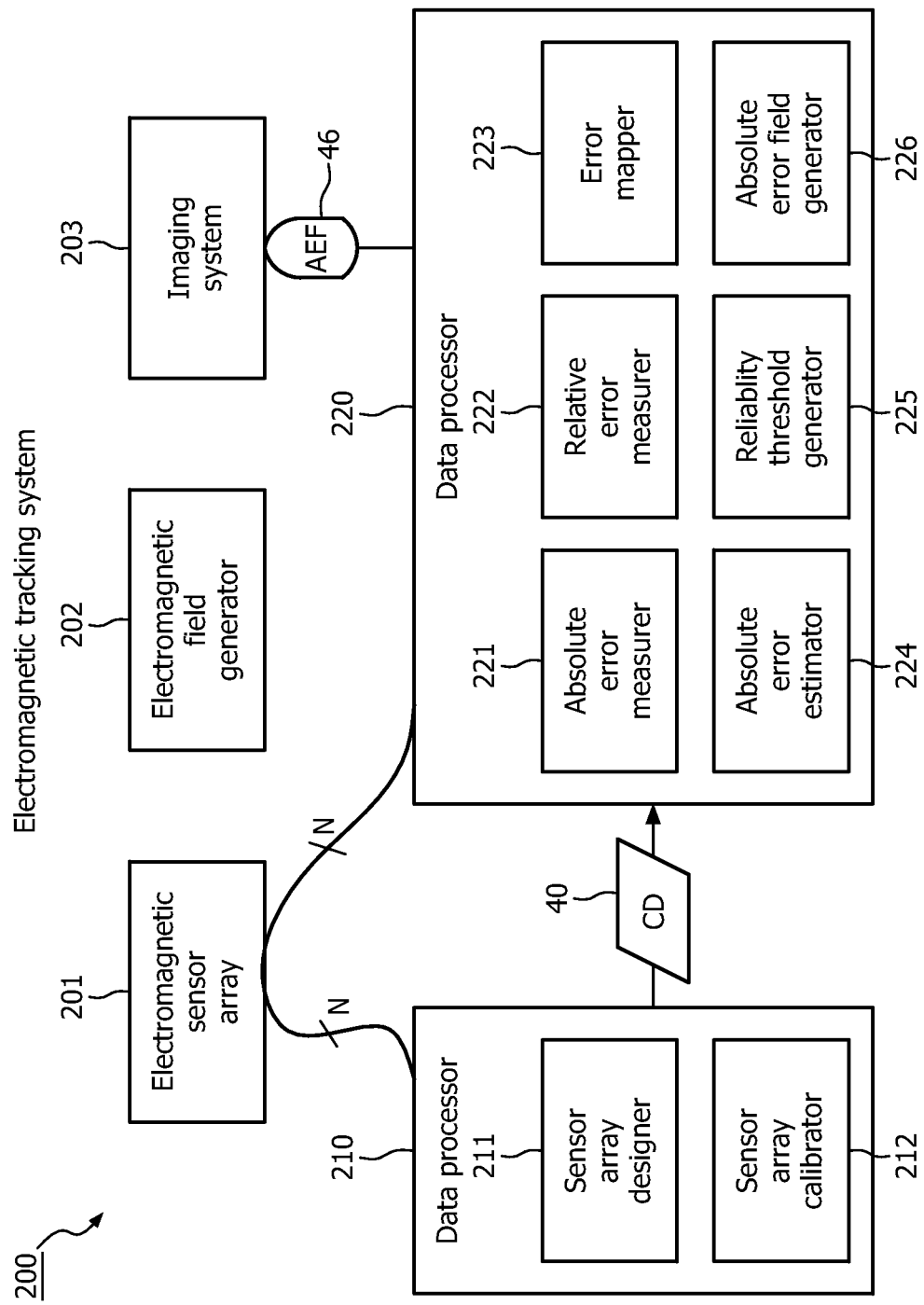
FIG. 19 illustrates an exemplary embodiment of a block diagram of an electromagnetic tracking system in accordance with the present invention.

FIG. 19 illustrates an electronic tracking system 200 employing an electromagnetic sensor array 201 incorporated with a calibration/surgical tool, an electromagnetic field generator 202, an imaging system 203, a data processor 210 and a data processor 220. Data processor 210 operates modules including sensor array designer 211 and a sensor array calibrator 212 for implementing calibration stage 60 shown in FIG. 4. Data processor 220 operates modules including absolute error measurer 221, a relative error measurer 222, an error mapper 223, an absolute error estimator 224, a reliability threshold generator 225 and an absolute error field generator 226 for implementing pre-operative stage 70 and intra-operative stage 80 as shown in FIG. 4. Electromagnetic sensor array 201 is connected to data processor 210 during calibration stage 60, and thereafter connected to data processor 220 during pre-operative stage 70 and intra-operative stage 80 with calibration data 40 generated by data processor 210 is communicated (e.g., uploaded or downloaded) to data processor 220.

The modules include software, hardware and/or firmware for executing various processes for characterizing and visualizing electromagnetic tracking errors in accordance with the present invention. To this end, data processor 210 includes one or more processors of any known type(s) and one more memories of any known type(s) to operate the modules. In practice, the modules may be individual modules within respective data processors as shown, or one or more of the modules may integrated within respective data processors. Furthermore, data processors 210 and 220 may be individual data processors as shown or integrated within one machine. Alternatively, intra-operative modules 224-226 may be installed within a different data processor than data processor 220 with calibration data 40 and error map 42 (FIG. 4) being communicated (e.g., uploaded or downloaded) to the data processor.

In practice, electromagnetic sensor array 201 may be rotated and/or pivoted at each measurement position of pre-operative stage 70 and/or each estimation position of intra-operative stage 80 to further enhance the for characterization and visualization of electromagnetic tracking errors in accordance with the present invention.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An electromagnetic tracking system, comprising:
an electromagnetic sensor array including at least two electromagnetic sensors arranged in a known geometrical configuration; and
a data processor in electrical communication with the electromagnetic sensor array to receive signals indicative of a sensing of an electromagnetic field by the electromagnetic sensors, the data processor including
a relative error measurer module operable to compute intra-operative relative errors responsive to a movement of the electromagnetic sensor array to numerous estimation positions within an intra-operative electromagnetic field,
wherein each intra-operative relative error is an absolute differential between a calibrated distance between an electromagnetic sensor pair and a sensed distance between the electromagnetic sensor pair within the intra-operative electromagnetic field, and
an absolute error estimator module operable to estimate intra-operative absolute errors responsive to a plotting of the intra-operative relative errors within a pre-operative error map representative of a statistical relationship between pre-operative absolute errors and pre-operative relative errors derived from a movement of the electromagnetic sensor array to numerous measurement positions within a pre-operative electromagnetic field,
wherein each pre-operative absolute error is an absolute differential between a measurement position of an electromagnetic sensor within the pre-operative electromagnetic field and a sensed position of an electromagnetic sensor within the pre-operative electromagnetic field, and
wherein each pre-operative relative error is an absolute differential between a calibrated distance and a sensed distance between an electromagnetic sensor pair within the pre-operative electromagnetic field.

2. The electromagnetic tracking system of claim 1,
wherein the data processor further includes an absolute error field generator module operable to generate an intra-operative absolute error field representative of an estimation of the intra-operative absolute errors.

3. The electromagnetic tracking system of claim 2, further comprising:
an imaging system in electrical communication with the data processor, wherein the imaging system is operable to visualize the intra-operative absolute error field.

4. The electromagnetic tracking system of claim 1,
wherein the data processor further includes an absolute error field generator module operable to generate an intra-operative absolute error field responsive to an estimation of the intra-operative absolute errors,
wherein the intra-operative absolute error field includes at least one of a reliable zone and an unreliable zone,
wherein the reliable zone is indicative of an undistorted area of the intra-operative electromagnetic field, and
wherein the unreliable zone is indicative of a distorted area of the intra-operative electromagnetic field.

5. The electromagnetic tracking system of claim 4, further comprising:
an imaging system in electrical communication with the data processor,
wherein the imaging system is operable to integrate the intra-operative absolute error field and ail Image of an object within the intra-operative electromagnetic field.

6. The electromagnetic tracking system of claim 1,
wherein the data processor further includes an absolute error field generator operable to generate an intra-operative absolute error field responsive to a comparison of a reliability threshold to an estimation of the intra-operative absolute errors,
wherein the intra-operative absolute error field including at least one of a reliable zone and an unreliable zone,
wherein the reliable zone is indicative of an undistorted area of the intra-operative electromagnetic field, and
wherein the unreliable zone being indicative of a distorted area of the intra-operative electromagnetic field.

7. The electromagnetic tracking system of claim 6, further comprising:
an imaging system in electrical communication with the data processor,
wherein the imaging system is operable integrate the intra-operative absolute error field and an image of an object within he intra-operative electromagnetic field.

8. The electromagnetic tracking system of claim 1, further comprising:
a calibration wherein e electromagnetic sensor array is incorporated in the calibration tool.

9. The electromagnetic tracking system of claim 1, further comprising:
a surgical tool, wherein the electromagnetic sensor array is incorporated in the surgical tool.

10. The electromagnetic tracking system of claim 9,
wherein the surgical tool includes a sheath; and
wherein the electromagnetic sensor array is patterned on an electronic substrate bonded to a surface of the sheath and covered with a barrier coating.

11. The electromagnetic tracking system of claim 9,
wherein the surgical tool includes a mandrin; and
wherein the electromagnetic sensor array is patterned on an electronic substrate bonded to a surface of the mandarin and covered with a barrier coating.

12. The electromagnetic tracking system of claim 9,
wherein the surgical tool includes a needle; and
wherein the electromagnetic sensor array is patterned on an electronic substrate bonded to a surface of the needle and covered with a barrier coating.

13. The electromagnetic tracking system of claim 9,
wherein the surgical tool includes a deflectable balloon; and
wherein the electromagnetic sensor array is patterned on an electronic substrate bonded to a surface of the deflectable balloon and covered with a barrier coating.

14. The electromagnetic tracking system of claim 9,
wherein the surgical tool includes a mesh; and
wherein the electromagnetic sensor array is patterned on an electronic substrate bonded to a surface of the mesh and covered with a barrier coating.

15. The electromagnetic tracking system of claim 1, further comprising:
an electromagnetic field generator operable to generate at least one of the pre-operative electromagnetic field and the intra-operative electromagnetic field.

16. An electromagnetic tracking method for a tool including a known geometrical configuration of an electromagnetic sensor array of two or more electromagnetic sensors, the electromagnetic tracking method comprising:

measuring a calibrated distance between at least one electromagnetic sensor pair responsive to the electromagnetic sensor array being within a calibration electromagnetic field;

controlling a movement of the electromagnetic sensor array within a pre-operative electromagnetic field to various measurement positions;

for each electromagnetic sensor, measuring a pre-operative absolute error at each measurement position of the electromagnetic sensor, wherein each pre-operative absolute error is an absolute differential between a measurement position and a sensed position of the electromagnetic sensor within die pre-operative electromagnetic field;

for each pairing of electromagnetic sensors, measuring a pre-operative relative error at each measurement position, wherein each pre-operative relative error is an absolute differential between a calibrated distance of an electromagnetic sensor paring and a sensed distance of the electromagnetic sensor pair within the pre-operative electromagnetic field;

generating a pre-operative error map derived from a statistical relationship between the pre-operative absolute errors and the pre-operative relative errors;

controlling a movement of the electromagnetic sensor array within an intra-operative electromagnetic field to various estimation positions;

for each electromagnetic sensor pair, measuring an intra-operative relative error at each estimation position, wherein each intra-operative relative error is an absolute differential between a calibrated distance between an electromagnetic sensor pair and a sensed distance of the electromagnetic sensor pair within the intra-operative electromagnetic field; and for each estimation position, estimating an intra-operative absolute error derived from a plotting of the intra-operative relative errors within the pre-operative error map.

17. The electromagnetic tracking method of claim 16, further comprising:

generating feedback representative of an estimation of the intra-operative absolute errors, wherein the feedback includes at least one of a visual feedback, an audio feedback and a tactile feedback.

18. The electromagnetic tracking method of claim 16, further comprising:

generating an intra-operative absolute error field responsive to an estimation of the intra-operative absolute errors,
  wherein the intra-operative absolute error field includes at least one of a reliable zone and an unreliable zone,
  wherein the reliable zone is indicative an undistorted electromagnetic area of the intra-operative electromagnetic field, and
  wherein the unreliable zone is indicative of a distorted electromagnetic area of the intra-operative electromagnetic field.

19. The electromagnetic tracking method of claim 16, further comprising:

integrating the intra-operative absolute error field and an image of an object within the intra-operative electromagnetic field.

20. The electromagnetic tracking method of claim 19, further comprising:

visualizing the integration of the intra-operative absolute error field and the image of the object within the intra-operative electromagnetic field.

* * * * *